United States Patent
Cree

(10) Patent No.: US 8,664,128 B2
(45) Date of Patent: Mar. 4, 2014

(54) ELASTIC LAMINATE AND METHOD OF MAKING

(75) Inventor: James W. Cree, Chesterfield, VA (US)

(73) Assignee: Advantage Creation Enterprise LLC, Chesterfield, VA (US)

( * ) Notice: Subject to any disclaimer, the term of this patent is extended or adjusted under 35 U.S.C. 154(b) by 603 days.

(21) Appl. No.: 12/362,740

(22) Filed: Jan. 30, 2009

(65) Prior Publication Data

US 2009/0191779 A1 Jul. 30, 2009

Related U.S. Application Data

(60) Provisional application No. 61/024,742, filed on Jan. 30, 2008.

(51) Int. Cl.
*B32B 5/02* (2006.01)

(52) U.S. Cl.
USPC ............ 442/328; 442/382; 442/394; 156/229; 156/494; 264/288.4; 264/288.8

(58) Field of Classification Search
USPC .................. 442/328, 382, 394; 156/229, 494; 264/288.4, 288.8
See application file for complete search history.

(56) References Cited

U.S. PATENT DOCUMENTS

| | | | |
|---|---|---|---|
| 3,719,736 A | 3/1973 | Woodruff | |
| 4,223,063 A | 9/1980 | Sabee | |
| 4,629,643 A | 12/1986 | Curro et al. | |
| 4,950,264 A | 8/1990 | Osborn, III | |
| 5,009,653 A | 4/1991 | Osborn, III | |
| 5,336,545 A | 8/1994 | Morman | |
| 5,368,909 A | 11/1994 | Langdon et al. | |
| 5,383,869 A | 1/1995 | Osborn, III | |
| 5,418,045 A | 5/1995 | Pike et al. | |

(Continued)

FOREIGN PATENT DOCUMENTS

| | | |
|---|---|---|
| EP | 0749739 B1 | 11/2000 |
| EP | 1712667 A1 | 10/2006 |
| WO | WO 98/55295 | 12/1998 |
| WO | WO 00/04215 | 1/2000 |

OTHER PUBLICATIONS

EPO Application No. 09706446.3 supplementary European Search Report (ESR), dated Jan. 6, 2012, pp. 1-7.

*Primary Examiner* — Andrew Piziali
*Assistant Examiner* — Jeremy R Pierce
(74) *Attorney, Agent, or Firm* — Hasse & Nesbitt LLC; Donald E. Hasse

(57) ABSTRACT

An elastic laminate for use as a tear resistant diaper side panel. The elastic laminate comprises an elastic substrate bonded to at least one layer of a tensioned spunbond nonwoven web comprising thermoplastic filaments comprising at least about 10% by weight polyethylene. The laminate is then incrementally stretched in the transverse direction to provide a service stretch greater than 100% and a strength ratio greater than 0.35. In one embodiment, the elastic substrate is bonded between the tensioned nonwoven webs by point bonding or hot melt adhesives. Also disclosed is a method for making an elastic laminate comprising the steps of providing at least one layer of a tensioned spunbond nonwoven web comprising thermoplastic filaments comprising at least about 10% by weight polyethylene, providing an elastic substrate, bonding the elastic substrate and the at least one layer of nonwoven web to provide an elastic laminate, and incrementally stretching the laminate in the transverse direction to provide a service stretch greater than 100% and a strength ratio greater than 0.35.

20 Claims, 4 Drawing Sheets

(56) References Cited

U.S. PATENT DOCUMENTS

| | | | |
|---|---|---|---|
| 5,422,172 A | 6/1995 | Wu | |
| 5,494,736 A | 2/1996 | Willey et al. | |
| RE35,206 E | 4/1996 | Hassenboehler, Jr. et al. | |
| 5,575,786 A | 11/1996 | Osborn, III | |
| 5,591,149 A | 1/1997 | Cree et al. | |
| 5,656,119 A | 8/1997 | Srinivasan et al. | |
| 5,674,216 A | 10/1997 | Buell et al. | |
| 5,851,935 A | 12/1998 | Srinivasan et al. | |
| 5,882,769 A * | 3/1999 | McCormack et al. | 428/152 |
| 6,015,764 A | 1/2000 | McCormack et al. | |
| 6,069,097 A | 5/2000 | Suzuki et al. | |
| 6,106,925 A | 8/2000 | Palumbo | |
| 6,190,602 B1 | 2/2001 | Blaney et al. | |
| 6,376,095 B1 | 4/2002 | Cheung et al. | |
| 6,395,211 B1 | 5/2002 | Dettmer et al. | |
| 6,537,644 B1 | 3/2003 | Kauschke et al. | |
| 6,610,904 B1 | 8/2003 | Thomas et al. | |
| 6,700,036 B2 | 3/2004 | Thomas et al. | |
| 6,703,115 B2 | 3/2004 | Hale et al. | |
| 6,720,279 B2 | 4/2004 | Cree et al. | |
| 6,752,947 B1 | 6/2004 | Lanigan et al. | |
| 6,849,319 B2 | 2/2005 | Cree et al. | |
| 6,942,748 B2 | 9/2005 | Cree et al. | |
| 6,942,896 B1 | 9/2005 | Martin | |
| 7,625,829 B1 * | 12/2009 | Cree et al. | 442/398 |
| 2003/0017345 A1 | 1/2003 | Middlesworth et al. | |
| 2004/0121687 A1 | 6/2004 | Morman et al. | |
| 2004/0161586 A1 | 8/2004 | Cree et al. | |
| 2005/0106980 A1 * | 5/2005 | Abed et al. | 442/395 |
| 2005/0124251 A1 | 6/2005 | Tsai et al. | |
| 2005/0241750 A1 * | 11/2005 | McCormack et al. | 156/229 |
| 2007/0029694 A1 | 2/2007 | Cree et al. | |
| 2007/0048498 A1 | 3/2007 | Cree | |
| 2007/0123124 A1 | 5/2007 | Middlesworth et al. | |
| 2007/0237924 A1 | 10/2007 | Bruce et al. | |
| 2007/0249253 A1 | 10/2007 | Angeli et al. | |
| 2007/0259154 A1 | 11/2007 | Cree | |

* cited by examiner

ELASTIC LAMINATE AND METHOD OF MAKING

CROSS-REFERENCE TO RELATED APPLICATION

This application claims the benefit of co-pending U.S. Provisional Application No. 61/024,742, filed Jan. 30, 2008.

TECHNICAL FIELD

This invention relates to a tear resistant elastic laminate suitable for use as a diaper side panel. The laminate comprises an elastic substrate bonded to at least one layer, and typically between two layers, of a tensioned spunbond nonwoven web comprising thermoplastic filaments comprising polyethylene. The laminate is then incrementally stretched in the transverse direction to provide a service stretch greater than 100% and a strength ratio greater than 0.35. The invention also relates to a method for making such an elastic laminate. In one embodiment, the laminate is used as a diaper elasticated ear.

BACKGROUND OF THE INVENTION

Nonwoven covered elastic fabrics are used in various industrial and consumer products sectors. In particular, webs of nonwoven elastic fabric are used to produce disposable sheets, disposable garments and hygiene and sanitary products, such as sanitary napkins, incontinence pads and baby diapers. However such webs typically do not have sufficient tear resistant strength to make them suitable for use as diaper side panels.

Several prior art patents describe different elastic fabric material that can be used for diaper side panels. For example, U.S. Pat. No. 5,674,216 to Buell et al describes the use of a zero strain laminate created by incremental stretching of laminate that has been assembled in the relaxed state. However, such a laminate may not have sufficient tear resistance for use in high stretch side panel applications.

Nonwoven covered elastic fabrics can be manufactured using various techniques. One process entails bonding, using hot melt adhesives or ultrasonics, a pre-made nonwoven of continuous filaments such as spunbond or discontinuous fibers (staple fibers) such as a thermobonded carded nonwoven, to an elastic film. The resulting laminate may be treated according to various techniques to yield an elastic laminate fabric. WO-A-9855295 describes a procedure for producing a composite material composed of two or three textile layers, wherein the fibers forming the textile layers are bonded and the layers are bonded to one another by means of a calender comprising a pair of engraved rollers. The rollers are produced and controlled for tip-to-tip operation, i.e. with all the protuberances of one roller in phase with the protuberances of the other roller, and form a pattern of bonding spots with a density corresponding to the density of the protuberances on the two rollers.

WO-A-0004215 describes a method for producing a nonwoven fabric by means of thermal consolidation of a web of fibers or filaments, such as a web of textile fibers, made of a thermoplastic material such as polypropylene. Bonding or consolidation is obtained through calendering with a roller provided with protuberances, which cooperates with a smooth roller.

U.S. Pat. No. 5,422,172 describes an elastic laminated sheet of an incrementally stretched nonwoven fibrous web and elastomeric film and a method of making the sheet. The elastic laminates are said to be useful in diapers, surgical gowns, sheets, dressing, hygienic products and the like.

While the above patents and applications disclose various methods for forming elastic laminates, many fall short of teaching a method to make an elastic laminate for diaper side panels that is tear resistant when subjected to high strain or stress. U.S. Pat. No. 6,942,748 describes an elastomeric film bonded between two or more layers of nonwoven webs formed of nonelastomeric thermoplastic fibers. The laminate is said to have in a predefined transverse direction, an elastic elongation value greater than the predefined elastic elongation value of the nonwoven webs, and an ultimate force to break in the predefined transverse direction of at least 3000 g/in. This patent provides higher weight nonwovens having high resistant to tearing, but teaches away from creating high stretch products using relatively low basis weight nonwovens. Since tear resistance is achieved by using highly bulked nonwovens, this process is not suitable for diaper side panels since it will inhibit anchoring the closure tape to the elastic film and require the use of a deadened zone to act as a linkage between the elastic laminate and the closure tape. Thus, there is a continuing need for an improved method to produce a diaper side elastic laminate having improved softness, compatibility with a tape closure, and high resistance to tearing.

SUMMARY OF THE INVENTION

The present invention relates to an elastic laminate comprising an elastic substrate bonded to at least one layer of a tensioned spunbond nonwoven web comprising thermoplastic filaments comprising at least about 10% by weight polyethylene, said laminate being incrementally stretched in the transverse direction to provide a service stretch greater than 100% and a strength ratio greater than 0.35.

In one embodiment, the elastic substrate is bonded by thermal bonding or glue between two highly tensioned nonwoven webs comprising continuous polyethyelene-containing filaments that are orientable under strain, before being incrementally stretched in the transverse direction. The invention also relates to a disposable diaper in which the side panel comprises the above high tear strength elastic laminate.

In another embodiment, the invention relates to a method for making an elastic laminate comprising the steps of:
 a. providing at least one layer of a tensioned spunbond nonwoven web comprising thermoplastic filaments comprising at least about 10% by weight polyethylene;
 b. providing an elastic substrate;
 c. bonding the elastic substrate and the at least one layer of nonwoven web to provide an elastic laminate; and
 d. incrementally stretching the laminate in the transverse direction to provide a service stretch greater than 100% and a strength ratio greater than 0.35.

The invention also relates to a method for making a tear resistant elastic laminate comprising the steps of:
 a. providing at least one layer of a tensioned spunbond nonwoven web comprising thermoplastic filaments comprising at least about 10% by weight polyethylene;
 b. providing an elastic substrate between the two layers of the nonwoven web;
 c. point bonding the elastic substrate and the layers of nonwoven web to provide an elastic laminate, wherein the bonding points are disposed in concentrated areas that are combined with areas having a substantially lower density of bonding points or the bonding points are individual bond sites distributed uniformly across the laminate; and d. incrementally stretching the laminate in the transverse direction to provide a service stretch greater than 100% and a strength ratio greater than 0.35.

DETAILED DESCRIPTION OF THE INVENTION

Figure 1:
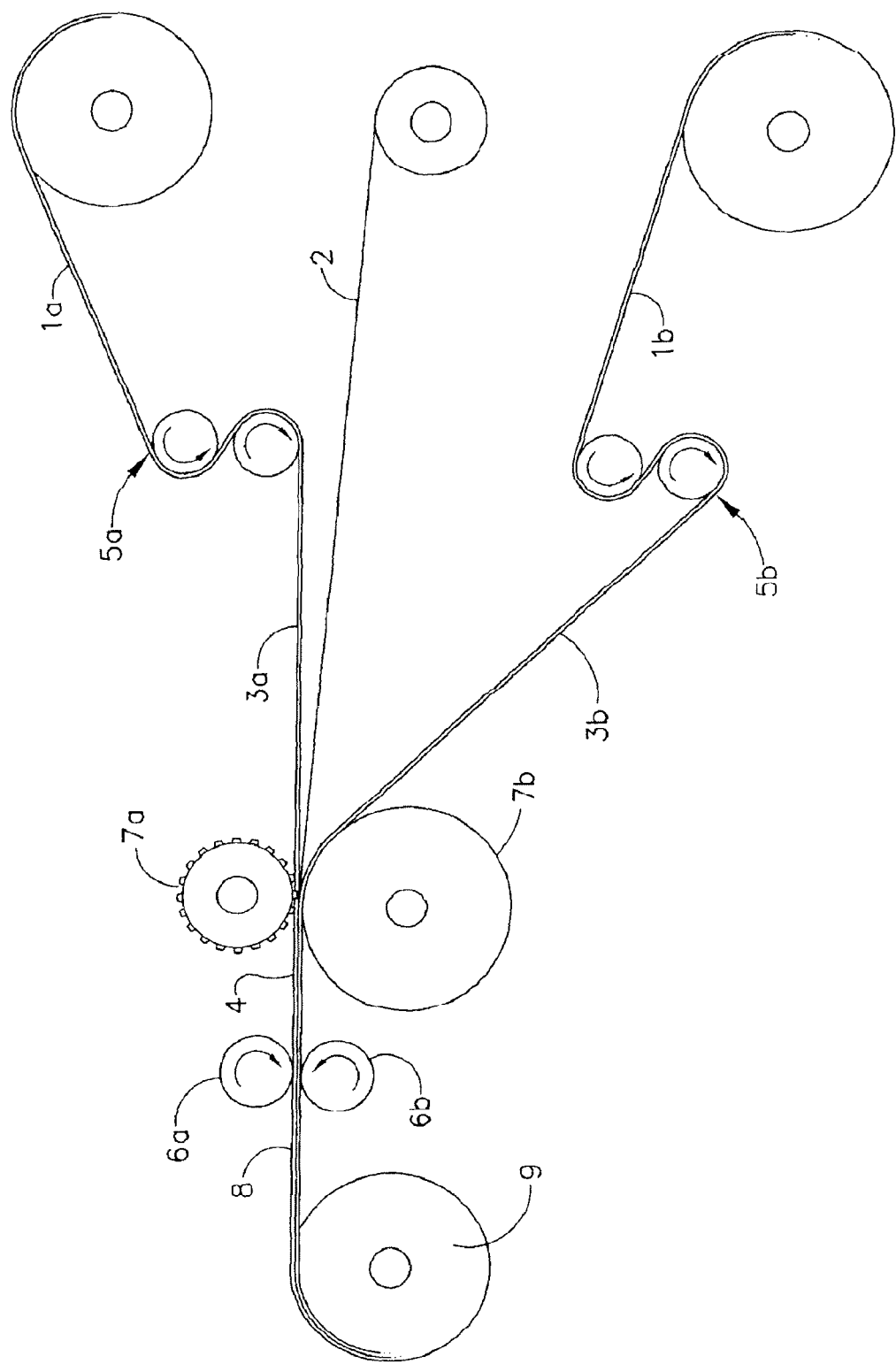
FIG. 1 is a diagram of a system for making an elastic laminate of the invention.

As used herein, the term "machine direction" means the direction in which precursor webs are formed, which is the longitudinal direction of an uncut web.

As used herein, the term "transverse direction" means the cross direction, disposed at 90° to the machine direction, and extends across the width of the precursor web.

As used herein, the term "relaxed state" means the only tension applied to the material is a low winding tension exhibited by the winder to prevent the web from getting stuck in the bonding nip.

As used herein, the term "tensioned state" means that the web is under machine direction strain or a combination of radiant heat and machine direction strain that forces it to shrink at least 10%, but less than 40%, in the transverse direction from its unsupported edges.

As used herein, the term "strength ratio" refers to the ultimate tensile tear strength in newtons per 2 linear inches of the laminate divided by the basis weight in $g/m^2$ of the laminate.

As used herein, the term "side panel" refers to any diaper elastic closure system where the material has a service stretch greater than or equal to 100%.

As used herein, the term "service stretch" refers to the amount of stretch and recovery a laminate is capable of undergoing without significant change in its stretch and recovery forces. For example, a service stretch of 100% means that a material one inch wide can stretch to 2 inches and return to 1 inch without significant change in the hysterisis forces.

The elastic laminate herein comprises an elastic substrate bonded to at least one layer, but typically bonded between two layers, of a tensioned spunbond nonwoven web. The spunbond nonwoven web comprises thermoplastic filaments comprising at least about 10%, typically at least about 20%, more typically at least about 50%, by weight, of polyethylene. For example, the filaments can be comprised of polyethylene or mixtures of polyethylene with polypropylene, polyester or biodegradable polylactic acid (PLA) fibers. The nonwoven web can be a web of continuous filaments, or a combination of filaments and fibers. The spunbond nonwoven web may include meltblown fibers. In one embodiment, the web is formed of continuous filament fibers that are bonded by bonding points distributed in a consistent pattern. The bonding points may be disposed in concentrated areas that are combined with areas having a substantially lower density of bonding points, or the bonding points may be individual bond sites distributed uniformly across the laminate. In one embodiment, in the nonwoven web, the bonded area ranges from about 1% to about 30% of the overall surface of the web. The nonwoven web prior to tensioning typically has a basis weight ranging from about 10 to about 40 $g/m^2$. Bonding methods, nonwoven webs and elastic substrates suitable for use herein are described in U.S. Patent Application Publication 2007/0249253 A1, incorporated herein by reference.

The filaments are typically bicomponent, meaning they are made by two immiscible polymer types and at least one of the polymers must be derived from an orientable low crystallinity type polymer such as polyethylene. The fibers can have a count ranging from about 1 to about 15 dtex. The filaments can be comprised of polyethylene or mixtures of polyethylene with polypropylene, polyester or biodegradable polylactic acid (PLA) fibers. For example, the following combinations can be used: polypropylene-polyethylene; polyester-polyethylene; polyester-copolyester-polyethylene, and PLA-coPLA-polyethylene. In general, the filaments can be produced with materials known and typically used to produce spunbond nonwoven fabrics that are consolidated using heat.

To produce the tensioned web, the nonwoven web is typically unwound from a roll and subjected to a high tensioning force and heat that forces it to undergo a controlled shrinkage in the transverse direction before bonding the web to the elastic substrate, for example an elastic film. The tensioning steps may be accomplished using any technology that forces the nonwoven web to neck in the transverse direction. In one embodiment, the web is run through S-rolls that can be either cold or heated, and the exit roll is running at a higher rotation speed then the entry roll. Another tensioning technique involves heating the web while running it through a battery of infrared heaters and applying extra winding tension to force the web to neck. Other known methods for inducing transverse direction necking of nonwovens may be used as long as the transverse direction shrinkage is greater than 10% and less than 40%, typically less than 30%.

The elastic laminate further comprises an elastic substrate bonded to at least one layer of tensioned nonwoven web. The elastic substrate typically is of the polyolefin type that is processable into a film or into a nonwoven web with filaments that are extruded by known direct fiber extrusion processes, such as spunbond or meltblown processes, or combinations thereof, for direct lamination by melt extrusion onto the fibrous web in one embodiment. Suitable elastomeric polymers may also be biodegradable or environmentally degradable. Suitable elastomeric polymers for the film or nonwoven include poly(ethylene-butene), poly(ethylene-hexene), poly(ethylene-octene), poly(ethylene-propylene), poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), poly(ethylene butylacrylate), polyurethane, poly(ethylene-propylene-diene), and ethylene-propylene rubber. Rubber-like polymers such as polyolefins produced from single-cite catalysts may also be employed. Catalysts known in the art as metallocene catalysts may be used, whereby ethylene, propylene, styrene and other olefins may be polymerized with butene, hexene, octene, etc., to provide elastomers suitable for use in this invention, such as poly(ethylene-butene), poly(ethylene-hexene), poly(ethylene-octene), poly(ethylene-propylene) and/or polyolefin terpolymers thereof. The elastic substrate typically has a gauge or thickness between about 0.25 and about 10 mils. In disposable applications, the elastic substrate thickness typically is from about 0.25 to about 2 mils.

In one embodiment, the elastic substrate may be a film formed of either a metallocene based low density polyethylene (m-LDPE), or a block-copolymer blend that contains styrene/butadiene/styrene (SBS), styrene/ethylene-butylene/styrene (SEBS), ethylene vinyl acetate (EVA), thermoplastic urethane, or cross-linked rubber. Typically, the elastic polymeric film has a basis weight of from about 18 g/m² to about 100 g/m². In one embodiment, an m-LDPE film has a basis weight of about 25 g/m², whereas block copolymer films have a basis weight of about 50 g/m². Also, it is desirable that the elastic polymeric films have less than 25% set when stretched 50%.

Bonding of the at least one layer of nonwoven web and the elastic substrate may be accomplished using various multi-layer bonding techniques, such as by adding a hot melt adhesive between the layers and then pressing the layers together. Alternatively, an ultrasonic bonding station or thermal pressure bonding may be used, as known in the art.

Figure 2:
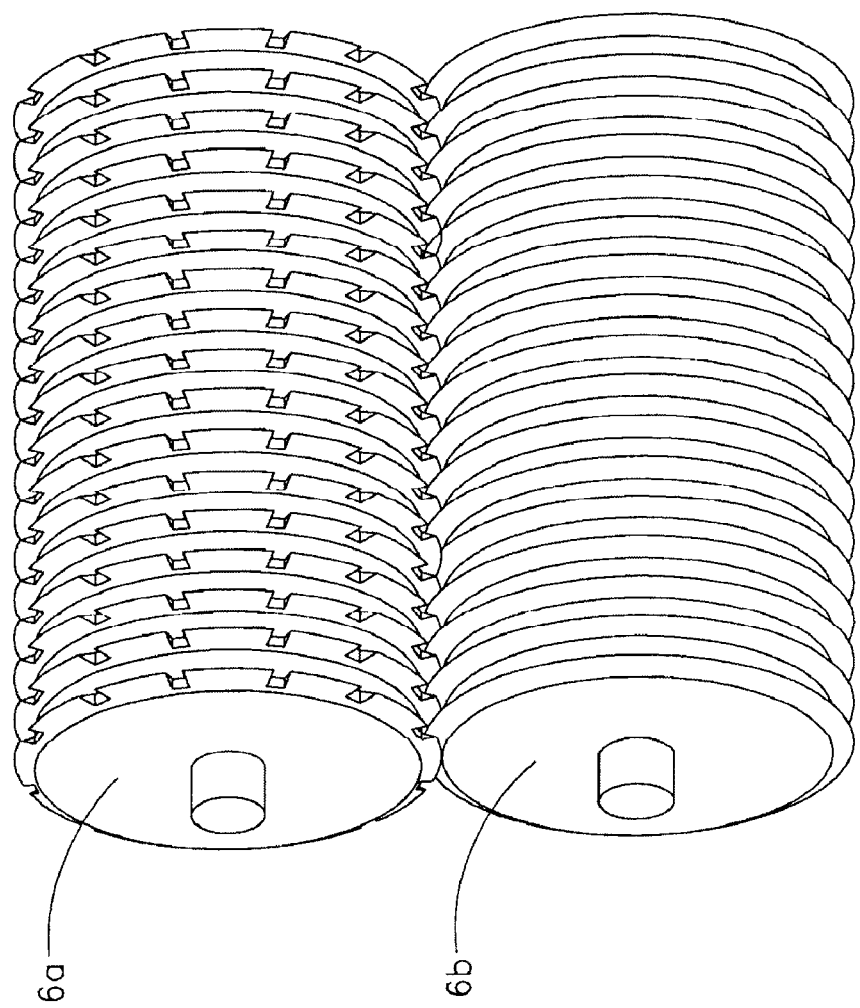
FIG. 2 is an enlarged view of the activation rollers 6a and 6b shown in FIG. 1.

FIG. 1 schematically shows a configuration of a line for producing a tear resistant elastic laminate according to the invention. In FIG. 1, two spunbond bicomponent (e.g., about 50% polyethylene/50% polypropylene) webs 1a and 1b are unwound from master rolls and then tensioned through S-rolls 5a and 5b that are rotating at different speeds to provide a transverse direction shrinkage of about 10% to 20%. The tensioned webs 3a and 3b are combined with the elastic substrate 2 which can be, for example, an elastic film. The layers are attached together by thermal bonding calender rolls 7, which includes heated calender rolls 7a and 7b. The product delivered from the calender 7 is a bonded or partially bonded, i.e. consolidated or partially consolidated, laminate that differs from thermally bonded laminates of the conventional type because its layers are joined to each other while the outer layer nonwoven webs are under tension. The resulting point bonded laminate 4 is then passed through a set of inter-digitizing rings 6 (FIG. 2 shows an enlarged view of these activation rollers 6a and 6b) that apply incremental stretch to the laminate in the transverse direction. The final laminate 8 of the invention is highly elastic in the transverse direction with strong force to break in the direction of incremental straining. The laminate has a service stretch greater than 100%, typically greater than 150%, more typically greater than 200%, and a strength ratio greater than 0.35, typically greater than 0.40. The final laminate 8 is then slit and wound on a roll for storage or shipment to customers.

In another embodiment, the laminate is formed by passing the tensioned nonwoven textile webs 3a and 3b and the elastic substrate 2 through an ultrasonic bonding nip instead of the thermal bonding calender 7 shown in FIG. 1. The three layers exit the nip as a single layer with the elastic substrate encapsulated permanently between the two webs 3a and 3b. The newly formed laminate is then mechanically incrementally stretched at the incremental stretching station, such as described above, to provide an elastic laminate having a service stretch and strength ratio as described above. The final laminate is then slit and wound on a roll for storage or shipment to customers.

The first and second nonwoven webs 1a and 1b typically are bicomponent spunbond webs, such as provided by Albis Corporation under the tradename Curatop™ SB. Spunbond nonwovens containing some percentage of continuous filament with polyethylene polymer origin will be suitable for this purpose. It is desirable that at least about 10% of the randomly disposed continuous filament fibers have approximately equal softening temperatures. The nonwoven webs are thus welded to the elastic film, typically by a combination of thermal and mechanical energy, to provide a peel force greater than 155 N/m (400 g/in).

Figure 3:
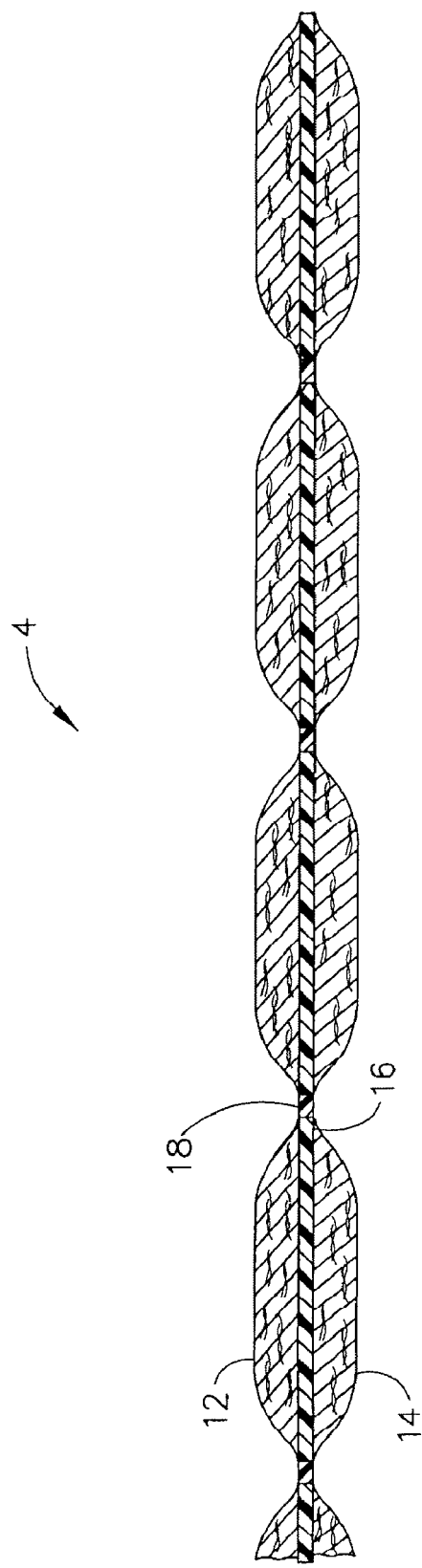
FIG. 3 is an enlarged schematic cross sectional view of the point bonded laminate 4 shown in FIG. 1.
Figure 4:
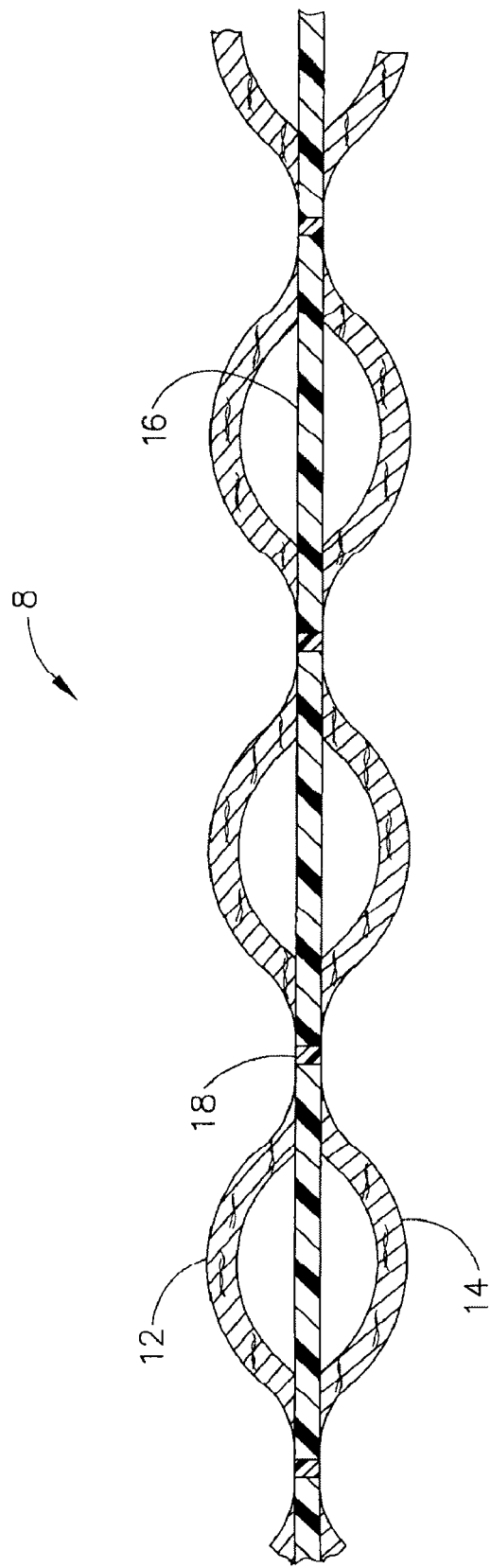
FIG. 4 is an enlarged schematic cross sectional view of the elastic laminate 8 of the invention shown in FIG. 1.

FIG. 3 is an enlarged cross sectional view from the machine direction (i.e., the section is along the transverse direction) of the point bonded laminate 4 shown in FIG. 1. In laminate 4, elastic substrate 16 is bonded to layers 12 and 14, each of which is a tensioned spunbond nonwoven web comprising thermoplastic filaments comprising at least about 10% by weight polyethylene. The layers are attached together by thermal bonding of the nonwoven webs 12 and 14 to the elastic substrate 16 at bond points 18 using heated calender rolls such as rolls 7a and 7b shown in FIG. 1. During the thermal bonding process, the teeth on roll 7a crush portions of layers 12, 16 and 14, compressing and melting them together at bond points 18. The resulting laminate 4 is then incrementally stretched in the transverse direction by passing it through a set of interdigitizing rings such as the activation rollers 6a and 6b shown in FIG. 2. An enlarged cross sectional view from the machine direction (i.e., the section is along the transverse direction) of the resulting elastic laminate 8 of the invention is shown in FIG. 4. The laminate 8 has a service stretch greater than 100% and a strength ratio greater than 0.35.

In addition to having good elasticity, it is also desirable that the elastic laminate be puncture resistant. For example, if the laminate is used to form pull tabs, or ears, for diaper products, it is important that the laminate not be easily punctured by long fingernails. Since nonwoven materials generally provide little or no puncture resistance, the elastic substrate or film should have a puncture resistance, as represented by a Dart Impact value, of at least 400 g.

The elastic laminate of the invention can be used as a component of a final article, such as a sanitary napkin, a baby diaper or the like. The laminate can also be subjected to further processes, such as a supplementary bonding process, an embossing process, a perforation process, or a combination of these. Furthermore, the bonded web may be joined to a plastic film or to another component to form a composite semi-finished material. This semi-finished product can be embossed or perforated, subjected to both embossing and perforation, or subject to other processes.

The following non-limiting example illustrates one embodiment of an elastic laminate of the invention.

An elastomeric film with a basis weight of 55 g/m² is obtained from the Clopay Corporation, Cincinnati Ohio. Two rolls of Curatop™ SB bicomponent (30% polyethylene/70% polypropylene) spunbond nonwoven web having a basis weight of 22 g/m² are obtained from Albis Corporation. Two rolls of consolidated nonwoven PP SMS (polypropylene spunbond-meltblown-spunbond) web having a basis weight of 27 g/m² sold under the tradename Elaxus™ are obtained from the Golden Phoenix Company, Taiwan. In a first experiment, one Curatop™ SB web is tensioned using high machine direction draw tension. The material necks 10% in the transverse direction. The tensioned material, the elastic film, and an untensioned Curatop™ SB web are then point bonded using a commercial Pantex point bonding pattern known as pattern 4 (a typical thermobonding pattern with raised embossing areas with about 30% coverage). After bonding, the resulting laminate is subjected to incremental mechanical stretching, resulting in a laminate of the invention having a service stretch of 200%. The incremental stretching is performed by a set of intermeshing gears such as described above. Once the laminate exits the intermeshing gears, it is wound on a roll. Samples are taken to measure the ultimate elongation and tear strength. In a second experiment, a heat pretensioned Elaxus™ web as described above is bonded to an elastic film. In this case, the laminate is mechanically stretched to deliver a service stretch of 200%. Samples from the two laminate rolls, and a sample of commercially available Tredegar Fabriflex™ 308 laminate, are stretched to break according to a modified ASTM D 882 test method. In this test, the width of the specimens is 2 inches instead of 1 inch (as per ASTM D 882). The elongation, tear strength, basis weight and strength ratio of the samples are as follows:

|  | Elongation at Break (%) | Tear strength (N/2 inches) | Basis Weight (g/m²) | Strength ratio Tear strength/ Basis weight |
|---|---|---|---|---|
| Laminate of invention with Curatop SB Bico Spunbond web | 453 | 39.4 | 97 | 0.41 |
| Laminate with Elaxus PP Spunbond web | 304 | 30.3 | 101 | 0.3 |
| Tredegar Fabriflex 308 | 378 | 43.3 | 145 | 0.3 |

The above results demonstrate that the Curatop™ SB laminate of the invention has the best balance of tear strength and basis weight. The high tear strength prevents premature tearing of the laminate when it is used as a side panel and the low basis weight allows better anchoring of the glue that is applied to hold the laminate to the fastener. The Elaxus™ and Fabriflex™ spunbond laminates fail to yield comparable results.

While particular embodiments of the present invention have been illustrated and described, various other changes and modifications can be made without departing from the spirit and scope of the invention. It is therefore intended to cover all such changes and modifications that are within the scope of this invention.

What is claimed is:

1. An elastic laminate comprising an elastic substrate bonded to at least one layer of a tensioned spunbond nonwoven web comprising thermoplastic bicomponent filaments consisting of polyethylene or mixtures of polyethylene with polypropylene, polyester or biodegradable polylactic acid, wherein at least about 10% by weight of each filament is polyethylene, wherein the nonwoven web prior to tensioning has a basis weight ranging from about 10 to about 40 g/m², said tensioned nonwoven web having transverse direction shrinkage greater than 10% and less than 30%, said laminate being incrementally stretched in the transverse direction to provide a service stretch greater than 100% and a strength ratio greater than 0.35.

2. An elastic laminate according to claim 1 wherein the nonwoven web is formed of continuous spunlaid filaments having a denier between 1 dtex and 3 dtex.

3. An elastic laminate according to claim 1 wherein the elastic substrate is a polyolefin film.

4. An elastic laminate according to claim 1 wherein the elastic substrate is polyolefin fibrous elastic made from meltblown or spunbond elastomer.

5. An elastic laminate according to claim 1 wherein in the nonwoven web, the bonded area ranges from about 1% to about 30% of the overall surface of the web.

6. An elastic laminate according to claim 1 wherein the nonwoven web is bonded to the elastic substrate using hot melt adhesive.

7. An elastic laminate according to claim 1 wherein the nonwoven web is bonded to the elastic substrate using ultrasonics.

8. An elastic laminate according to claim 1, said tensioned nonwoven web having transverse direction shrinkage greater than 10% and less than 20%.

9. A method for making an elastic laminate comprising the steps of:
1) providing at least one layer of a tensioned spunbond nonwoven web comprising thermoplastic bicomponent filaments consisting of polyethylene or mixtures of polyethylene with polypropylene, polyester or biodegradable polylactic acid, wherein at least about 10% by weight of each filament is polyethylene, wherein the nonwoven web prior to tensioning has a basis weight ranging from about 10 to about 40 g/m², said tensioned nonwoven web having transverse direction shrinkage greater than 10% and less than 30%;
2) providing an elastic substrate;
3) bonding the elastic substrate and the at least one layer of tensioned nonwoven web to provide an elastic laminate; and
4) incrementally stretching the laminate in the transverse direction to provide a service stretch greater than 100% and a strength ratio greater than 0.35.

10. A method for making an elastic laminate according to claim 9 wherein the nonwoven web is formed of continuous spunlaid filaments having a denier between 1 dtex and 3 dtex.

11. A method for making an elastic laminate according to claim 9 wherein the elastic substrate is a polyolefin film.

12. A method for making an elastic laminate according to claim 9 wherein in the nonwoven web, the bonded area ranges from about 1% to about 30% of the overall surface of the web.

13. A method for making an elastic laminate according to claim 9 wherein the nonwoven web is bonded to the elastic substrate using hot melt adhesive or using ultrasonics.

14. A method for making an elastic laminate according to claim 9, said tensioned nonwoven web having transverse direction shrinkage greater than 10% and less than 20%.

15. A method for making a tear resistant elastic laminate comprising the steps of:
1) providing at least two layers of a tensioned spunbond nonwoven web comprising thermoplastic bicomponent filaments consisting of polyethylene or mixtures of polyethylene with polypropylene, polyester or biodegradable polylactic acid, wherein at least about 10% by weight of each filament is polyethylene, wherein the nonwoven web prior to tensioning has a basis weight ranging from about 10 to about 40 g/m², said tensioned nonwoven web having transverse direction shrinkage greater than 10% and less than 30%;
2) providing an elastic substrate between the at least two layers of the nonwoven web;
3) point bonding the elastic substrate and the at least two layers of tensioned nonwoven web to provide an elastic laminate, wherein the bonding points are disposed in concentrated areas that are combined with areas having a substantially lower density of bonding points or the bonding points are individual bond sites distributed uniformly across the laminate; and
4) incrementally stretching the laminate in the transverse direction to provide a service stretch greater than 100% and a strength ratio greater than 0.35.

16. A method for making an elastic laminate according to claim 15 wherein the nonwoven web is formed of continuous spunlaid filaments having a denier between 1 dtex and 3 dtex.

17. A method for making an elastic laminate according to claim 16 wherein the elastic substrate is a polyolefin film.

18. A method for making an elastic laminate according to claim 17 wherein the nonwoven web is bonded to the elastic substrate using hot melt adhesive or using ultrasonics.

19. A disposable diaper in which the side panel comprises an elastic laminate comprising an elastic substrate bonded to at least one layer of a tensioned spunbond nonwoven web comprising thermoplastic bicomponent filaments consisting of polyethylene or mixtures of polyethylene with polypropylene, polyester or biodegradable polylactic acid, wherein at least about 10% by weight of each filament is polyethylene, wherein the nonwoven web prior to tensioning has a basis weight ranging from about 10 to about 40 g/m², said tensioned nonwoven web having transverse direction shrinkage greater than 10% and less than 30%, said laminate being incrementally stretched in the transverse direction to provide a service stretch greater than 100% and a strength ratio greater than 0.35.

20. A disposable diaper according to claim 19 wherein the elastic laminate is incrementally stretched in the transverse direction to provide a service stretch greater than 200% and a strength ratio greater than 0.40.

* * * * *